(12) United States Patent
Miyazawa et al.

(10) Patent No.: US 6,584,858 B1
(45) Date of Patent: Jul. 1, 2003

(54) DEVICE AND METHOD FOR MEASURING ADHESIVE STRENGTH

(75) Inventors: Yasunao Miyazawa, Tokyo (JP);
Tsutomu Noshiroya, Tokyo (JP);
Takao Kimijima, Kodaira (JP); Takao Kokubu, Kodaira (JP)

(73) Assignees: Lintec Corporation, Tokyo (JP);
Bridgestone Corporation, Tokyo (JP)

( * ) Notice: Subject to any disclaimer, the term of this patent is extended or adjusted under 35 U.S.C. 154(b) by 0 days.

(21) Appl. No.: 09/979,122

(22) PCT Filed: Mar. 13, 2001

(86) PCT No.: PCT/JP01/01931
§ 371 (c)(1),
(2), (4) Date: Nov. 19, 2001

(87) PCT Pub. No.: WO01/75418
PCT Pub. Date: Oct. 11, 2001

(30) Foreign Application Priority Data

Apr. 4, 2000 (JP) .................................. 2000-102559
Jul. 19, 2000 (JP) .................................. 2000-219084

(51) Int. Cl.[7] .......................... G01N 3/08; G01F 17/00
(52) U.S. Cl. ..................... 73/827; 73/150 A; 73/150 R
(58) Field of Search .......................... 73/827, 150 A, 73/829, 150 R

(56) References Cited

U.S. PATENT DOCUMENTS

| | | | | |
|---|---|---|---|---|
| 2,751,784 A | * | 6/1956 | Gershberg | 73/150 A |
| 3,793,879 A | * | 2/1974 | Fowler | 73/827 |
| 4,888,985 A | * | 12/1989 | Siemer | 73/150 A |
| 4,893,503 A | * | 1/1990 | Kimura et al. | 73/150 A |
| 5,311,768 A | * | 5/1994 | Seib et al. | 73/54.22 |

FOREIGN PATENT DOCUMENTS

| | | | | |
|---|---|---|---|---|
| JP | 53-95692 | | 8/1978 | |
| JP | 56114737 A | * | 9/1981 | G01L/5/00 |
| JP | 144344/1981 | | 10/1981 | |
| JP | 57063435 A | * | 4/1982 | G01N/19/04 |
| JP | 57064144 A | * | 4/1982 | G01N/19/04 |
| JP | 57090140 A | * | 6/1982 | G01N/19/04 |
| JP | 57184951 A | * | 11/1982 | G01N/19/04 |
| JP | 2-2532 | | 1/1990 | |
| JP | 8-166340 | | 6/1996 | |
| JP | 08166340 A | * | 6/1996 | G01N/19/04 |

\* cited by examiner

*Primary Examiner*—Hezron Williams
*Assistant Examiner*—Lilybett Martir
(74) *Attorney, Agent, or Firm*—Lowe Hauptman Gilman & Berner, LLP

(57) ABSTRACT

First, a sample holder 13, 57 is lowered such that a sample is held. Next, a roller 11 or a plate-shaped member 56 is lowered and pressed to an adhesive surface 15A of a sample 15. At this time, a tape 23 is disposed between the roller 11 or the plate-shaped member 56 and the adhesive surface 15A of the sample 15, and a fixed pressure load is applied to the sample 15. Then after a fixed period of time has passed, the tape 23 is pulled from the sample 15 by the raising of the roller 11 or the plate-shaped member 56 and an adhesive strength is measured with a load cell 25 according to the tension of the tape 23 at that time. After measuring, a take-up reel 21, 52 is rotated so as to wind up a predetermined pitch of the tape 23, and an unused portion of the tape 23 is reeled out to the tip of the roller 11 or the plate-shaped member 56.

4 Claims, 10 Drawing Sheets

DEVICE AND METHOD FOR MEASURING ADHESIVE STRENGTH

TECHNICAL FIELD

The present invention relates to a measuring method and device for measuring the adhesive strength of a sample of rubber or the like.

RELATED ART

Conventionally, an adhesive strength measuring device for measuring the adhesive strength of a sample by pressing a probe as a contact member comprising a part of adhesive strength measuring means to a sample, then separating the probe from the sample, and measuring the force applied to a probe with a load cell has been known (Japanese Patent Publication No. HEI 2-2532).

With the foregoing type of conventional device, because the probe directly contacts the sample, the probe becomes contaminated such that it requires cleaning after each measuring which is bothersome. In addition, there was the problem that the next measurement value may be effected if it is not cleaned sufficiently.

DISCLOSURE OF THE INVENTION

In order to solve the foregoing problems, according to the present invention, there is provided an adhesive strength measuring method for measuring an adhesive strength of a sample by pressing a predetermined point of a contact member provided with a predetermined contact surface to a sample, then peeling the pressed contact surface, and measuring the adhesive strength, wherein after part of the contact surface has been pressed to the sample, an unused portion of the contact surface is pressed to a next sample.

Also, there is provided an adhesive strength measuring method for measuring an adhesive strength of a sample by pressing a tape as a contact member to a sample, then separating the tape from the sample, and measuring the adhesive strength to the tape, wherein the tape is disposed between a guide member around which the tape is wound, and the sample, and the tape is moved such that an unused portion of the tape becomes positioned between the guide member and the sample for each measurement.

Further according to the present invention, there is provided an adhesive strength measuring device for measuring an adhesive strength of a sample by pressing a predetermined point of a contact member provided with a predetermined contact surface to a sample, then peeling the pressed contact surface, and measuring the adhesive strength, wherein a structure is employed which has moving means for moving an unused portion of the contact surface to a position in which the sample is able to be pressed for each measurement of the adhesive strength.

Also, there is provided an adhesive strength measuring device for measuring an adhesive strength of a sample by pressing a tape to a sample, then separating the tape from the sample, and measuring the adhesive strength to the tape, wherein a structure is employed in which moving means is provided for moving the tape positioned between the guide member around which the tape is wound and the sample.

Moreover, the foregoing structure may further be provided with sample holding means for holding the sample.

The sample holding means is provided so as to be able to be raised and lowered at the same time as the guide member, and is also provided so as to be able to be raised and lowered relative to the guide member via urging means for urging in a direction away from the guide member.

The moving means may comprise a supply portion around which the tape is wound, a take-up portion for winding the tape, and a driving portion for driving the take-up portion. Here, the supply portion and the take-up portion may be provided with a cassette member which is attachable and detachable with respect to the device body.

Note that in this specification, "contact member" is used as a concept which includes tapes as well as other members having a contact surface which can be pressed to the sample. Also, "unused portion of the contact surface" means a portion of a contact surface other than the contact surface of the contact member which has been pressed to a sample once.

BRIEF DESCRIPTION OF THE DRAWINGS

FIG. 1-B is a schematic view showing a state in which a sample holder 13 is pressed to an adhesive surface 15A of a sample 15;

FIG. 1-C is a schematic view showing a state in which a tape 23 is pressed to the adhesive surface 15A of the sample 15;

FIG. 5-B is a schematic view showing a state in which a sample holder 57 is contacting the adhesive surface 15A of the sample 15;

FIG. 5-C is a schematic view showing a state in which the tape 23 is pressed to the adhesive surface 15A of the sample 15;

BEST MODE FOR CARRYING OUT THE INVENTION

Figure 1:
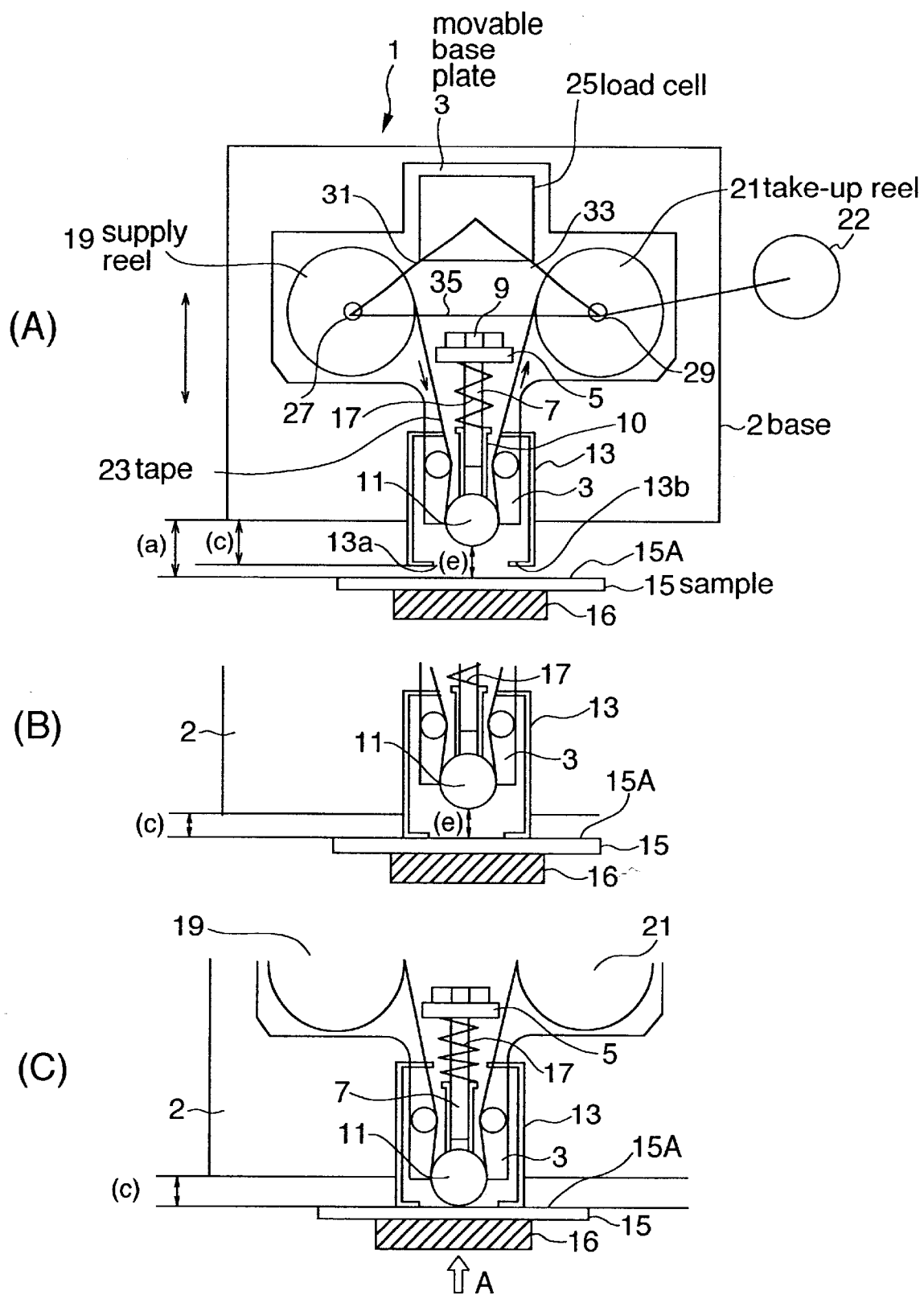
FIG. 1-A is an elevation view of an adhesive strength measuring device according to a first embodiment, which is a schematic view showing a state prior to starting of the measuring operation.
Figure 2:
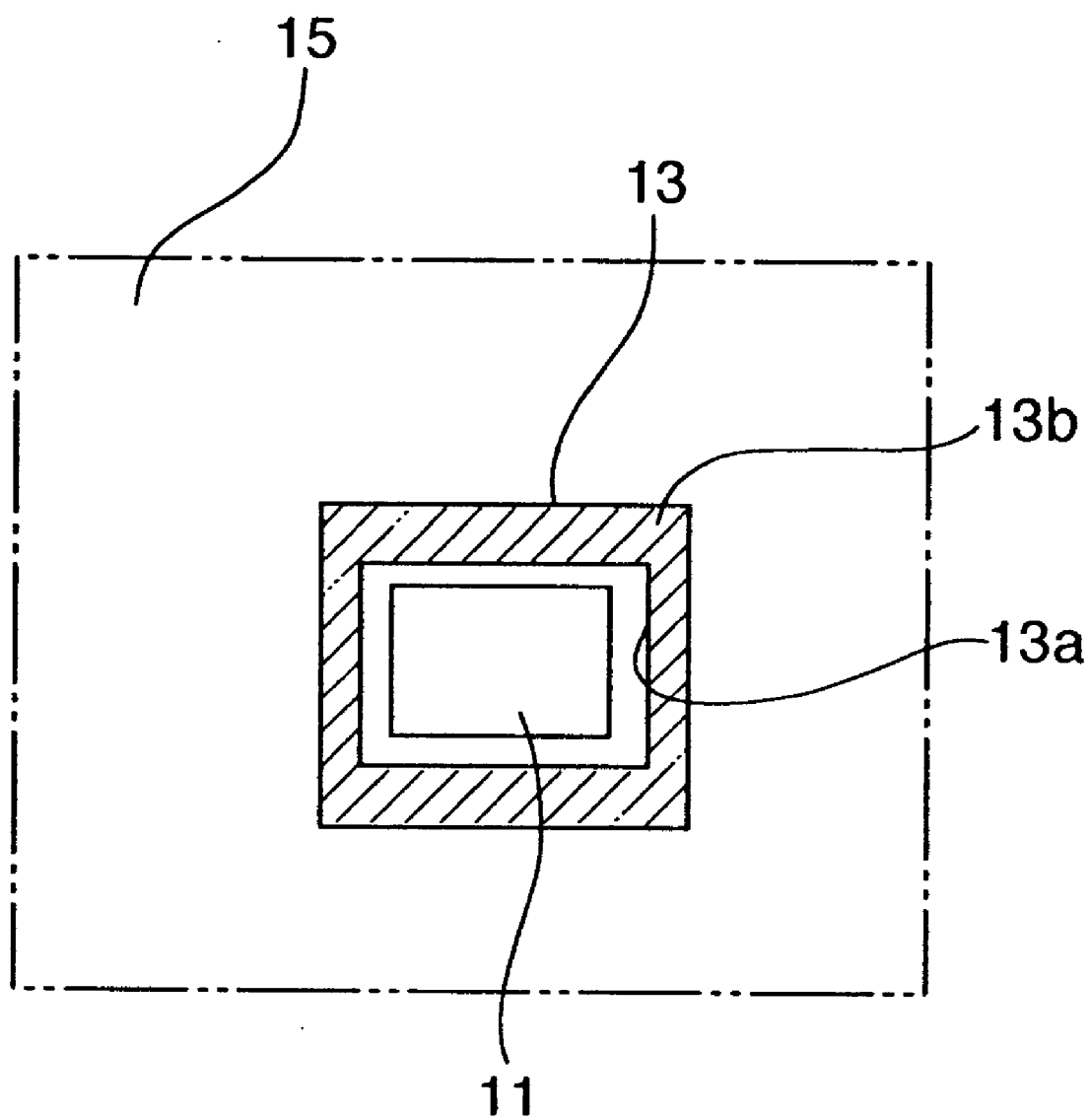
FIG. 2 is a schematic view of a roller 11 and the sample holder 13 as viewed from the direction of Arrow A in FIG. 1-C.
Figure 3:
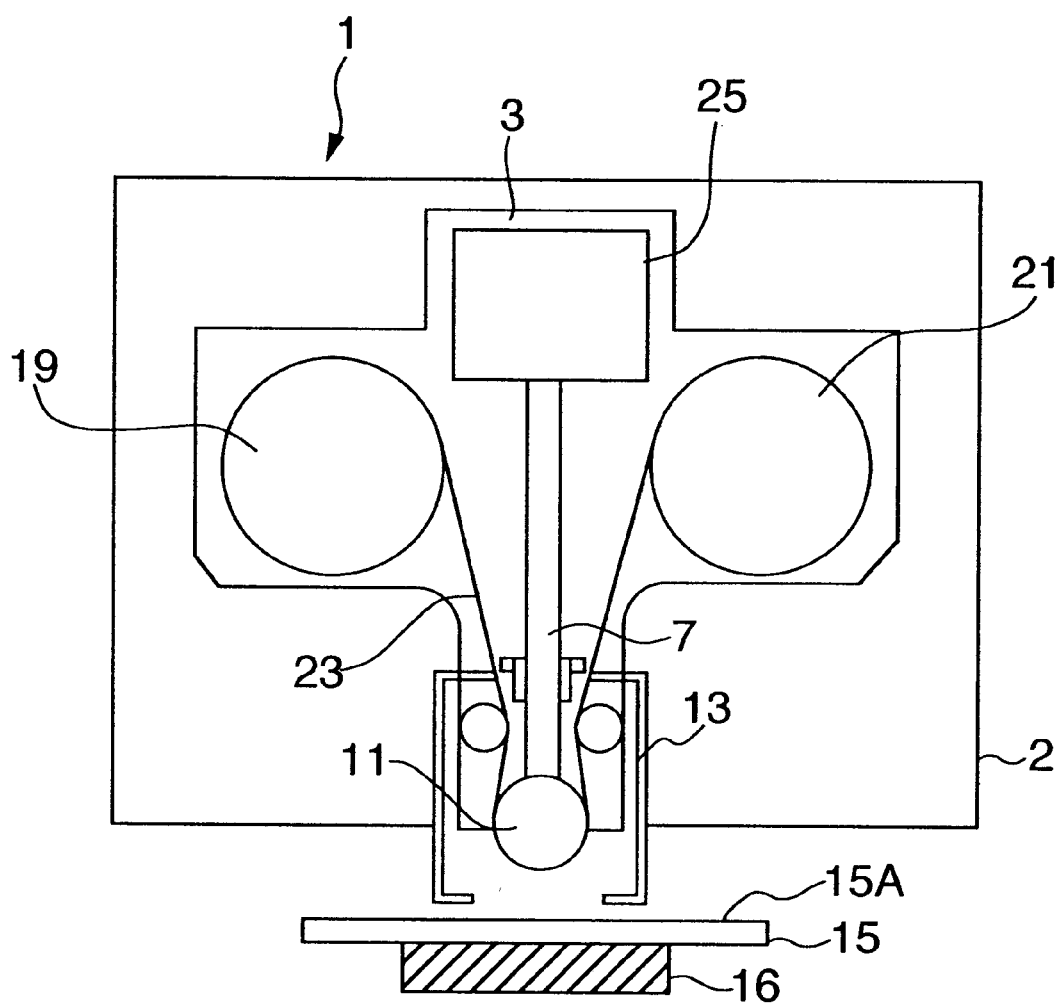
FIG. 3 is a side view showing a modification of the first embodiment.

FIG. 1 is a schematic view showing a first embodiment of the present invention. In an adhesive strength measuring device 1, a movable base plate 3 mounted so as to be able to be raised and lowered by a motor, not shown, is mounted to a base 2, and a guide member support body 7 is mounted and fixed to a mounting plate 5 with a nut 9 on the movable base plate 3. On the tip of the guide member support body 7, a roller 11, as a guide member around which antifouling tape (hereinafter referred to simply as "tape") 23 as a contact member in place of a conventional probe is wound, is rotatably attached. The roller 11 is disposed in a box-shaped sample holder 13. FIG. 2 is a view of the sample holder 13 as viewed from below. An opening 13a is formed in a lower portion of the sample holder 13, and the periphery of this opening 13a is a flange portion 13b for holding a sample (rubber or the like) 15 having an adhesive surface 15A on a surface. Also, the sample 15 is placed on a sample platform 16 comprising a rigid plate material.

A coil spring 17 is positioned between an upper surface of a spring seat 10 fixed to the roller 11 and the mounting plate 5, and the roller 11 is urged downward by the coil spring 17.

A supply reel 19 as a supply portion and a take-up reel 21 as a take-up portion are disposed on both the left and right sides of the mounting plate 5 in FIG. 1-(A), and the tape 23 is wound around the supply reel 19. This tape 23 is strung around the roller 11 on the tip portion of the spring seat 10 of the guide member support body 7 fixed to the mounting plate 5, and is wound around the take-up reel 21. The take-up reel 21 is driven by a stepping motor (or a servo motor or the like) 22 as a driving portion. Both reels 19, 21 are provided with a brake mechanism (not shown) for inhibiting rotation thereof, and provided with a mechanism for fixing the tape 23 so that it can not move. The tape 23 is composed of, for example, polyethylene terephthalate (PET) or the like, but is not particularly limited to that material. As long as the material has tensile rigidity against an adhesive strength of the adhesive surface 15A of the sample 15, a tape composed of, for example, metal, paper, or other plastic material or the like may be used. Moving means is provided by the supply reel 19, take-up reel 21, and stepping motor 22.

A load cell 25 as measuring means is disposed above the supply reel 19 and the take-up reel 21. A mounting shaft 27 of the supply reel 19 and a mounting shaft 29 of the take-up reel 21 are each connected to the load cell 25 by rods 31, 33, respectively. Further, each mounting shaft 27, 29 is connected by a rod 35 and these are disposed on the movable base plate 3.

Hereinafter, operation of the foregoing adhesive strength measuring device 1 will be described.

First, in a state as shown in FIG. 1-(A) in which the sample 15 is provided on the sample platform 16, when a start button, not shown, is pushed, the base 2 is lowered by driving means, not shown. Accordingly, the sample holder 13 disposed on the base 2 is lowered such that the adhesive surface 15A of the sample 15 is pressed and held by the flange portion 13b of the sample holder 13 (FIG. 1-(B)). Next, the movable base plate 3 is lowered a predetermined distance at a fixed speed by driving means, not shown, such that the roller 11 presses on the adhesive surface 15A of the sample 15 as shown in FIG. 1-(C). At that time, the tape 23 abuts against the roller 11, as mentioned above, such that the tape 23 becomes in a pressed state between the roller 11 and the adhesive surface 15A of the sample 15. When the roller 11 is lowered only a predetermined distance (e) (FIGS. 1-(A), (B)) by lowering the movable base plate 3 and the tape 23 reaches the adhesive surface 15A, driving is stopped. The coil spring 17 is compressed (FIG. 1-(C)) and the fixed pressure load against the urging of the coil spring 17 is applied to the sample 15, and further, the pressure load is applied for only a fixed period of time set beforehand.

When the movable base plate 3 is raised at a fixed speed in a state in which the flange portion 13b of the sample holder 13 is pressing and holding the adhesive surface 15A of the sample 15 after pressure has been applied to the sample 15 for a fixed period of time, the contact surface of the tape 23 which has been pressed to the sample 15 is then peeled from the adhesive surface 15A of the sample 15, and the tape 23 pressed to the roller 11 then receives a peeling force according to the adhesive strength of the adhesive surface 15A. At this time, rotation of the supply reel 19 and the take-up reel 21 is inhibited by a brake medium, not shown, so that the tape 23 does not move. Therefore, the tension applied to the tape 23 is applied to the respective mounting shafts 27, 29 of the supply reel 19 and the take-up reel 21, and the tension applied to these mounting shafts 27, 29 is detected by the load cell 25 via a support body of three points, being rods 31, 33, 35. That is, the peeling force of the adhesive surface 15A of the sample 15 is measured by the load cell 25 via the tape 23. At this time, the peeling force is determined with an output signal of the load cell 25 by a control device, not shown.

A detected value of the peeling force reaches a peak value when the tape 23 separates from the sample 15. The control device detects this peak value as the adhesive strength of the sample 15, outputs the measurement data, and displays OK (good) on a monitor, not shown, if the peak value is within a predetermined range and displays NG (poor) if outside the predetermined range.

After the peak value is detected, the roller 11 returns to the upper limit position by raising of the movable base plate 3 (FIG. 1-(B) (e)). After measuring is complete, when the base 2 is raised by means of a driving device, not shown, and the sample holder 13 fixed to the base 2 is raised and reaches a raised position (FIG. 1-(A) (a), (e)), a brake, not shown, of the supply reel 19 and take-up reel 21 is released and the stepping motor 22 is driven so as to rotate the take-up reel 21 and wind up the tape 23 at a predetermined pitch so that an unused portion of the tape 23 abuts with the roller 11 while being reeled out, and measurement is completed.

With the above-mentioned control device, the following items may be set as general functions.

(1) Pressing speed control when pressing, and peeling speed control when peeling, the tape 23 abutted with the roller 11 with respect to the sample 15.
(2) Measurement of the pressure load (pressure energy) of the tape 23 to be abutted with the roller 11 with respect to the sample 15.
(3) Setting of the pressure load time of the tape 23 to be abutted with the roller 11 with respect to the sample 15.
(4) Measurement of the peeling force (peeling energy) with respect to the sample 15.
(5) Feeding pitch setting of the tape 23.
(6) Setting of the permissible range of the peeling force and determination of the measurement results.
(7) Other drive control etc.

As mentioned above, according to the first embodiment, the tape 23 is pressed via the roller 11 to the sample 15 having a surface adhesion while being reeled out in each case. Therefore, the tape 23 does not become contaminated by the adhesive surface 15A of the sample 15, making it possible to accurately measure the adhesive strength of a new sample 15 to be measured the next time.

Also, in the first embodiment, the load cell 25 detects the force applied to the respective mounting shafts 27, 29 of the supply reel 19 and the take-up reel 21. However, it is not limited to this; the guide member support body 7 may be directly connected to the load cell 25 and the roller 11 (FIG.

3) such. that the pressure force and the peeling force applied to the sample 15 may be detected.

Next, a second embodiment of the present invention will be described. In the following description, the same reference characters will be used for structural portions which are the same or equivalent to those in the first embodiment, and descriptions thereof will be omitted or simplified.

Figure 4:
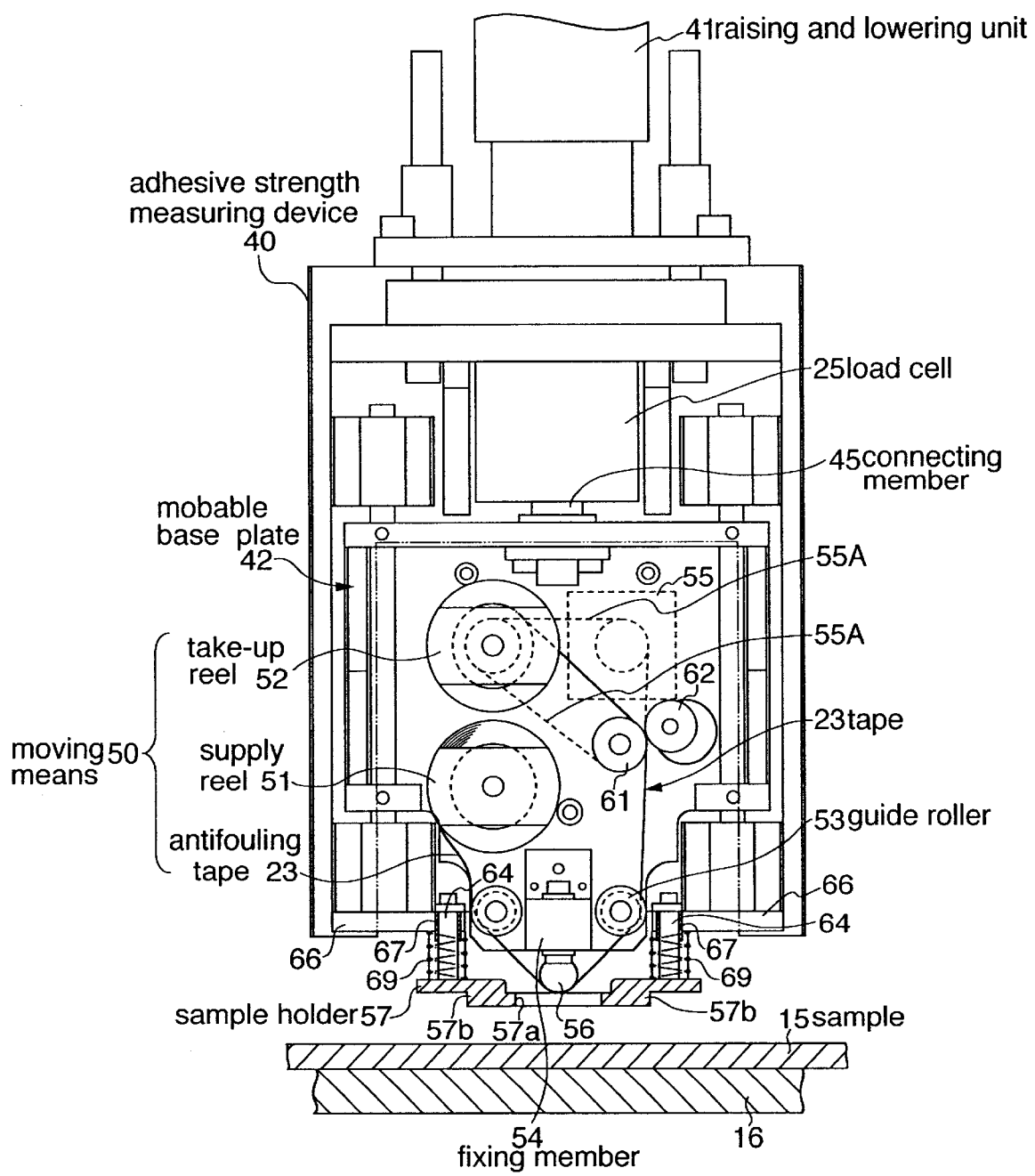
FIG. 4 is a schematic elevation view of an adhesive strength measuring device according to a second embodiment.

FIG. 4 is a schematic elevation view of an adhesive strength measuring device 40 according to the second embodiment. In this figure, the adhesive strength measuring device 40 comprises a movable base plate 42 provided so as to be able to be raised and lowered by a raising and lowering unit 41 such as a single shaft robot, a load cell 25 for connecting this movable base plate 42. and the raising and lowering unit 41, a supply reel 51 as a supply portion and a take-up reel 52 as a take-up portion fixed to the movable base plate 42, a stepping motor (or a servo motor or the like) 55 as a driving portion for driving the take-up reel 52, a plate-shaped member 56 as a guide member fixed to the lower end side of the movable base plate 42, and a plate-shaped sample holder 57 disposed below this plate-shaped member 56.

The same tape 23 as in the first embodiment is wound around the supply reel 51, and this tape 23 is strung around the tip of the plate-shaped member 56 via a guide roller 53 so as to be wound up on the take-up reel 52. A driving roller 61 around which the tape 23 between the plate-shaped member 56 and the take-up reel 52 is strung is provided below the stepping motor 55. The tape 23 strung around this driving roller 61 is forcefully pressed by a spring or the like, not shown, to the side of the driving roller 61 with a nip roller. Further, by the driving of the stepping motor 55, the take-up reel 52 and the driving roller 61 are able to be simultaneously rotated by a timing belt 55A wound between pulleys, not shown, respectively attached to each of these and a side of a shaft, not shown, of the stepping motor 55. By the rotation of these, the tape 23 is reeled out intermittently from the supply reel 51 at predetermined lengths and only the amount of tape 23 reeled out is able to be wound up on the take-up reel 52. Just as in the first embodiment, on the supply reel 51 and the take-up reel 52, a brake mechanism (not shown) for inhibiting the rotation thereof is provided such that the tape 23 is able to be fixed so as not to be able to move at a predetermined timing. Here, moving means 50 generally comprises a supply reel 51, take-up reel 52, stepping motor 55, and a driving roller 61.

In substantially the center of the sample holder 57 is formed an opening 57a through which the plate-shaped member 56 is able to pass, and the periphery of that opening 57a is made to be a flange portion 57b for pressing the sample (rubber or the like) 15. Also, in FIG. 4 on both the left and right sides of the sample holder 57, a rod 64 is provided standing such that slidable contact is possible. This rod 64 is inserted through a cylindrical member 67 attached to a support member 66 which is connected to the lower end side of the movable base plate 42, and is able to move relatively in the vertical direction with respect to the cylindrical member 67. Therefore, in addition to being able to be raised and lowered simultaneously with the plate-shaped member 56 fixed to a fixing member 54 following raising and lowering of the movable base plate 42, the sample holder 57 is movable relative to the plate-shaped member 56. Note that the width of the plate-shaped member 56 of this embodiment is set so as to be substantially the same or slightly narrower with respect to the tape width of the tape 23. Here, a compression coil spring 69 as urging means is disposed between the sample holder 57 and the support member 66. The sample holder 57 is urged downward, that is, in a direction away from the plate-shaped member 56, by the compression coil spring 69. Accordingly, from an initial state (FIG. 4) in which the tip of the plate-shaped member 56 is positioned above the opening 57a of the sample holder 57, when an upward force against the urging force of the compression coil spring 69 acts on the sample holder 57, the tip of the plate-shaped member 56 is able to appear and disappear from the opening 57a.

Next, operation of the adhesive strength measuring device 40 according to the present embodiment will be described.

Figure 5:
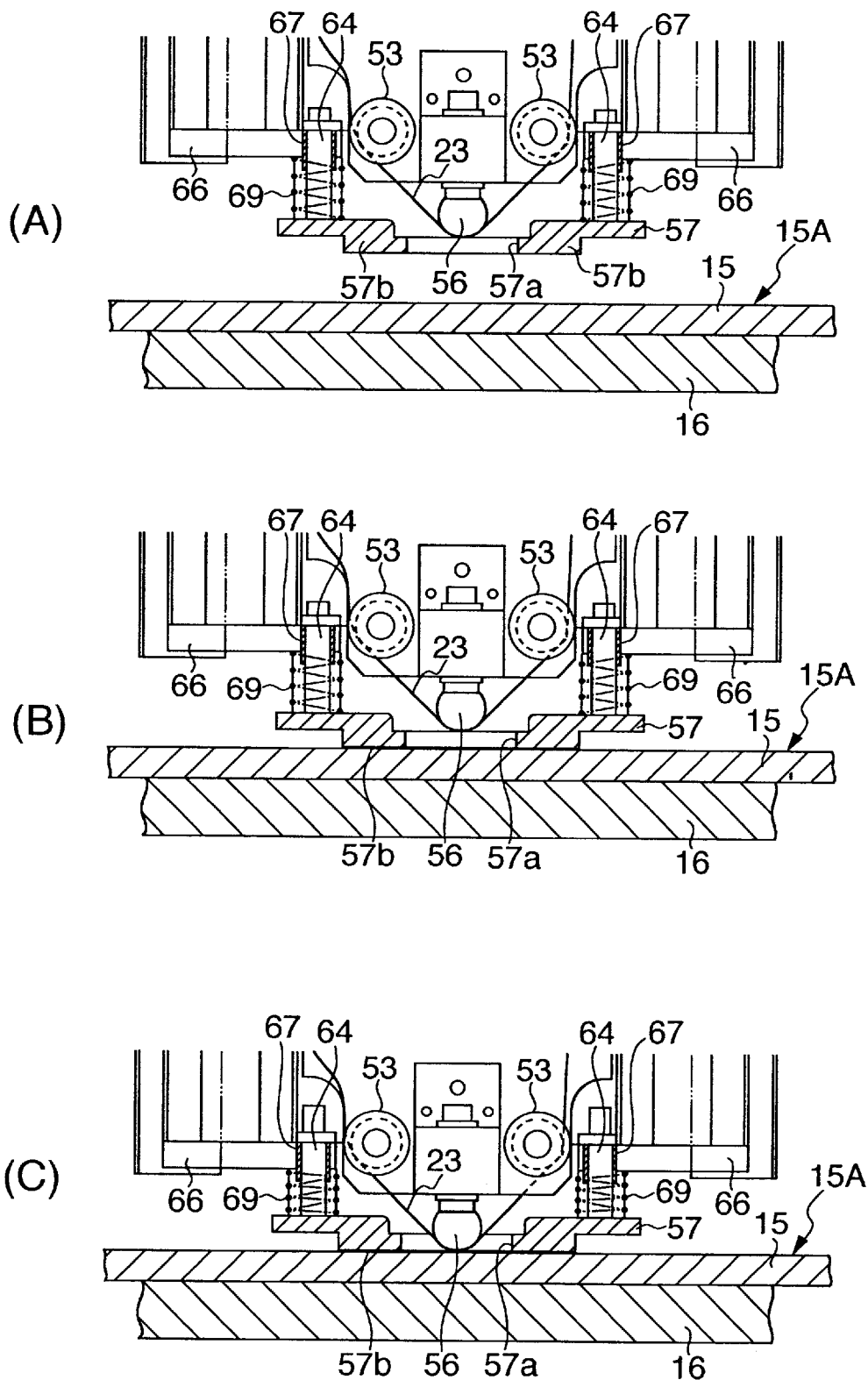
FIG. 5-A is a schematic view showing a state prior to starting of the measuring operation.
Figure 6:
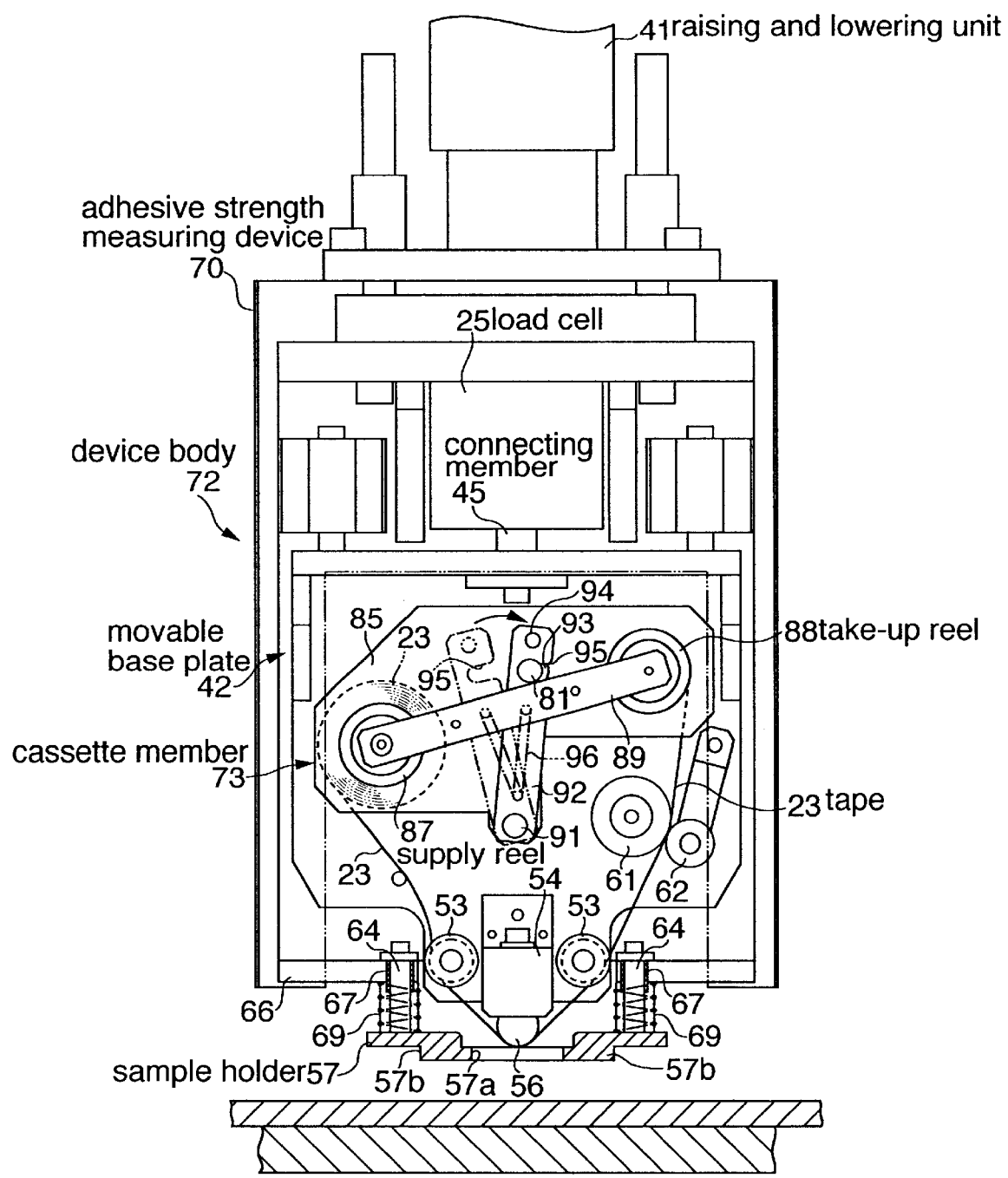
FIG. 6 is a schematic elevation view of an adhesive strength measuring device according to a third embodiment.

First, in a state as shown in FIG. 5-(A) in which the sample 15 is placed on the sample platform 16, when the start button, not shown, is pushed, the movable base plate 42 lowers by means of a raising and lowering unit 41, and while the tip of the plate-shaped member 56 as a tape guide member is in a position above the opening 57a, the plate-shaped member 56 and the sample holder 57 are lowered toward the sample 15. Then, the flange portion 57b of the sample holder 57 is contacted with the adhesive surface 15A of the sample 15 (FIG. 5-(B)). Moreover, when the movable base plate 42 is lowered, the compression coil spring 69 is compressed, and the plate-shaped member 56 is lowered with respect to the sample holder 57 so that the tip of the plate-shaped member 56 appears from the opening 57a and a fixed pressure load is applied for a fixed period of time to the adhesive surface 15A of the sample 15 (FIG. 5-(C)). At this time, driving of the raising and lowering unit 41 stops so that the tape 23 strung around the tip of the plate-shaped member 56 is in a state pressed between the plate-shaped member 56 and the adhesive surface 15A of the sample 15. At the same time, the flange portion 57b of the sample holder 57 is pressed and held to the adhesive surface 15A of the sample 15 by the urging force of the compression coil spring 69.

After the pressure load has been applied to the sample 15 for a fixed period of time, the movable base plate 42 is raised to the initial position at a fixed speed by means of the driving of the raising and lowering unit 41. At this time, the tape 23 which was pressed to the adhesive surface 15A of the sample 15 receives a peeling stress from the adhesive strength of the adhesive surface 15A. Here, the supply reel 51 and the take-up reel 52 are inhibited by the brake mechanism, not shown, such that the tape 23 will not move. In this manner, just as with the first embodiment, the tension applied to the tape 23, that is, the peeling stress of the adhesive surface 15A, is detected by the load cell 25 via a connecting member 45. The peak value of that peeling stress is the adhesive strength of the sample 15, and a predetermined numerical value of the adhesive strength is determined with a control device (not shown), just as in the first embodiment, according to an output signal from the load cell 25. When this is complete, the brake mechanism (not shown) of the supply reel 51 and the take-up reel 52 is released and the stepping motor 55 is driven such that the take-up reel 52 and the driving roller 61 are rotated to wind up the tape 23 at a predetermined pitch. An unused portion of the tape 23 is then reeled out to the tip of the plate-shaped member 56, and measurement is completed.

In the above manner, according to the second embodiment, in addition to the effect in the first embodiment, it is possible to press a plate-shaped member 56 to the sample 15 while holding the sample 15 using the sample holder 57 by only driving the raising and lowering unit 41 with one single shaft robot or the like, and thus simplify the drive system of the device.

Next, a third embodiment of the present invention will be described using FIGS. 6 through 10. In the following description, the same reference characters will be used for structural portions which are the same or equivalent to those in the first and second embodiments, and descriptions thereof will be omitted or simplified.

With an adhesive strength measuring device 70 according to the third embodiment, the holding structure of the tape 23 is different from that of the adhesive strength measuring device 40 of the second embodiment. The other structure is substantially the same as that of the adhesive strength measuring device 40. In other words, the adhesive strength measuring device 70 is characterized in that the cassette member 73 that holds the tape 23 is attachable and detachable with respect to the device body 72.

Figure 7:
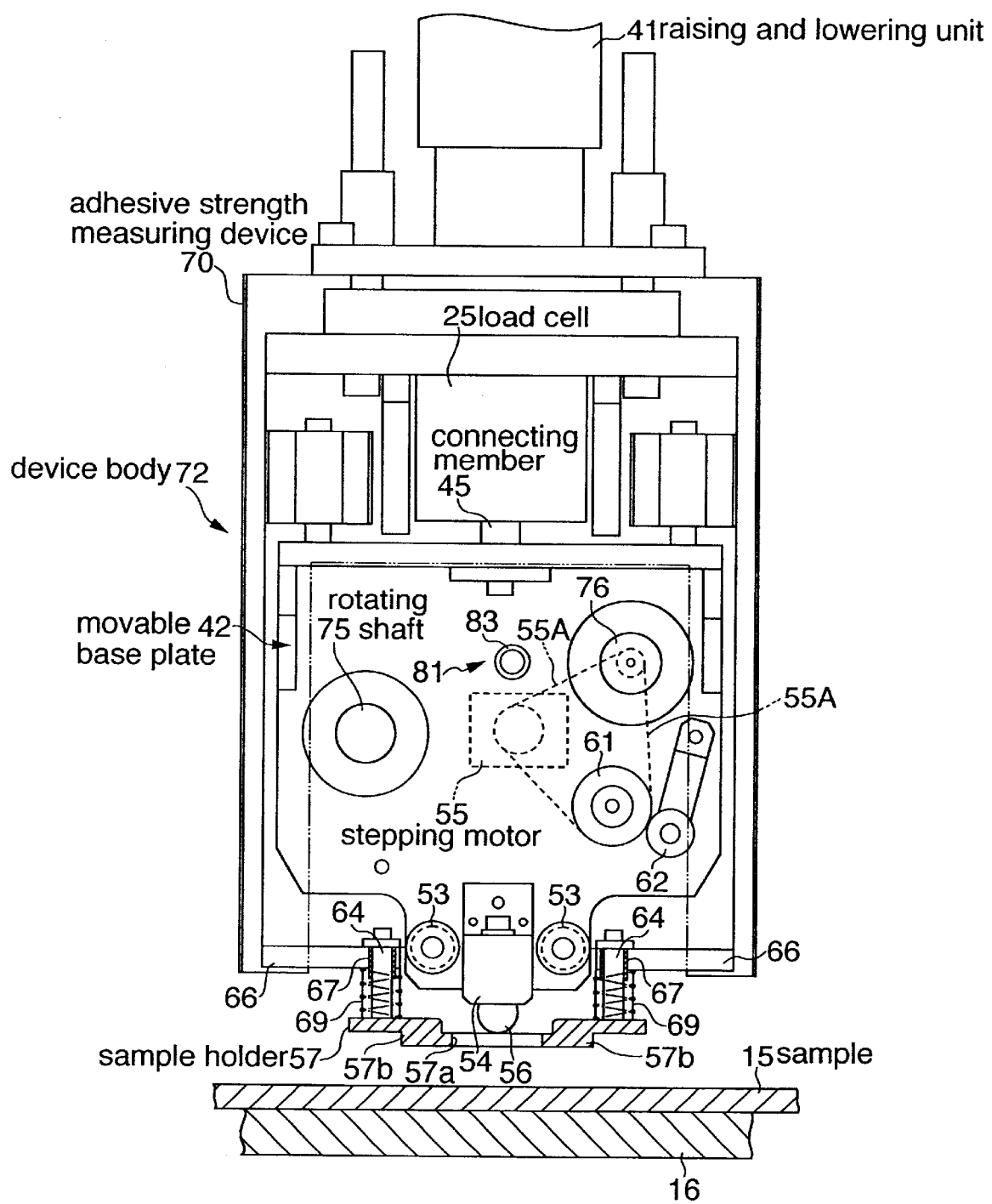
FIG. 7 is a schematic view showing a state in which a cassette member 73 has been removed from the adhesive strength measuring device in FIG. 6.

The device body 72 is structured such that rotating shafts 75, 76 positioned on both the left and right sides of the movable base plate 42 in the FIG. 7, in place of the supply reel 51 and the take-up reel 52, and an engaging pin 81 that protrudes between each of the rotating shafts 75, 76 are newly provided on the adhesive strength measuring device 40 of the aforementioned second embodiment.

The timing belt 55A is strung around the rotating shaft 76 on the right side in FIG. 7 on the back side (the back side as viewed in the same figure) of the movable base plate 42, such that it is able to rotate simultaneously with the driving roller 61 positioned below the rotating shaft 76 by driving the stepping motor 55.

Figure 8:
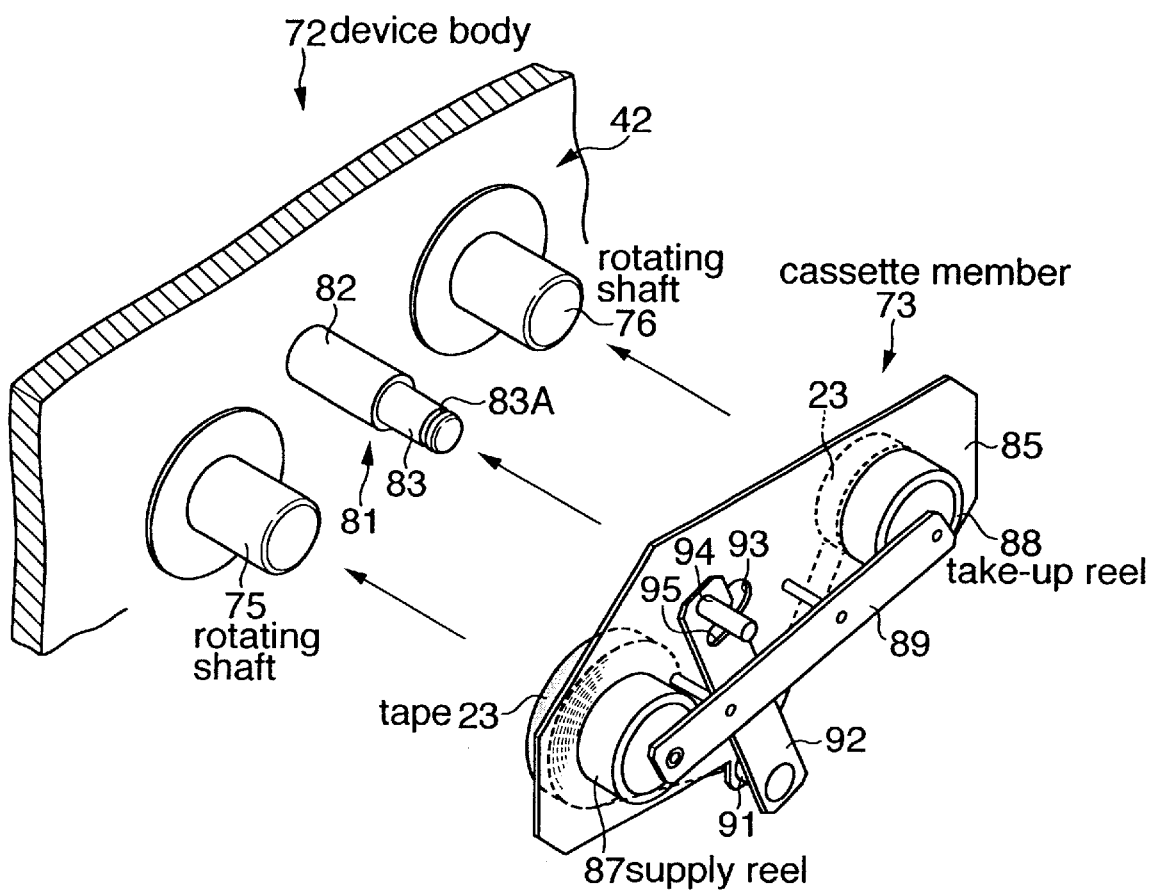
FIG. 8 is an exploded perspective view of essential portions in FIG. 6.
Figure 9:
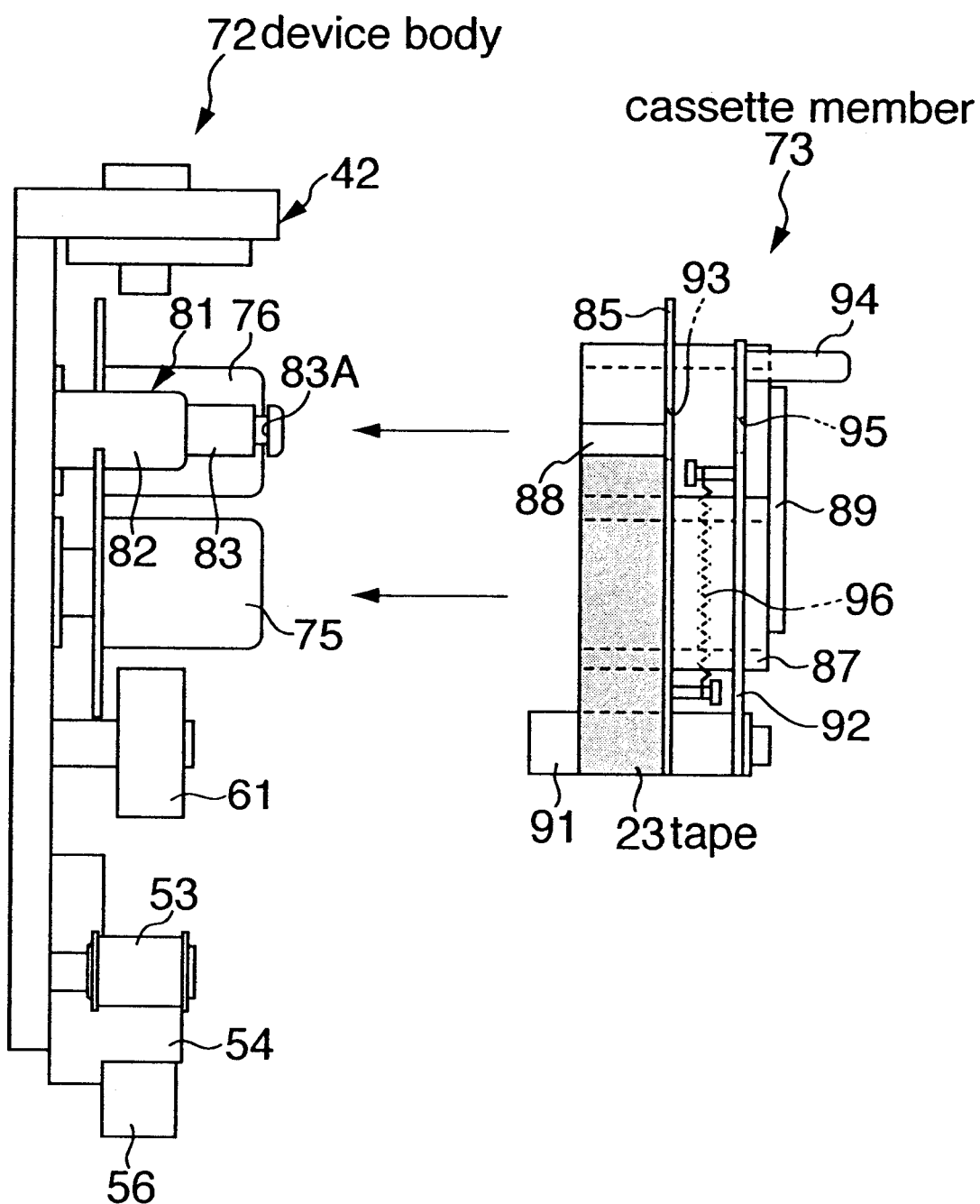
FIG. 9 is a schematic side elevation view of essential portions of a device body 72, showing a state prior to mounting of the cassette member 73.
Figure 10:
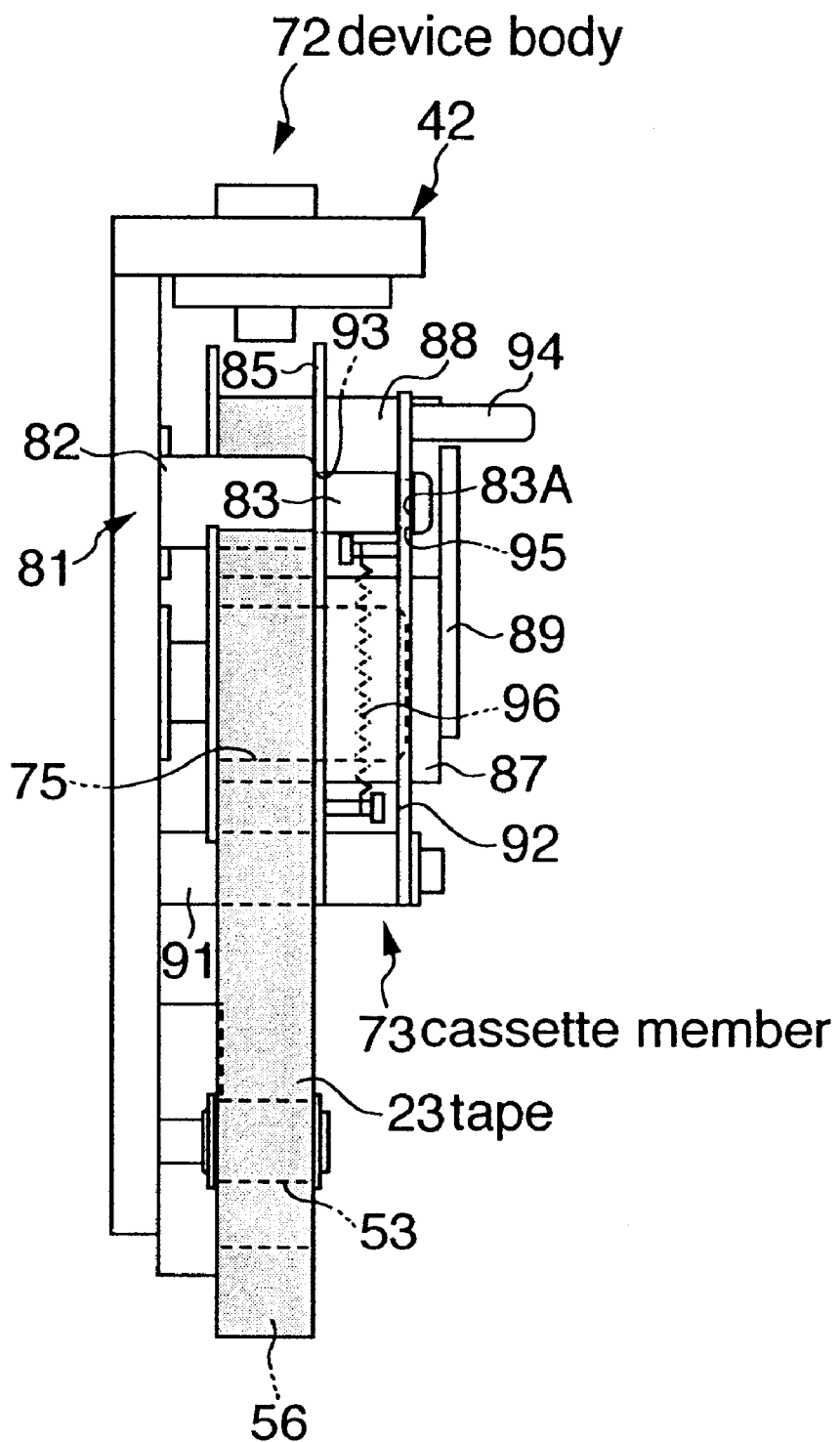
FIG. 10 is a schematic side elevation view of essential portions of the device body 72, showing a state in which the cassette member 73 has been mounted.

As shown in FIG. 8 through FIG. 10, the engaging pin 81 is constructed of a base portion 82 on the side of the movable base plate 42 and a tip portion 83 which is connected to this base portion 82 and which also has a smaller diameter than the base portion 82. A circular groove shaped neck portion 83A is formed in a portion of the outer periphery of the tip portion 83.

The cassette member 73 is provided with a plate-shaped base 85 having a flat surface positioned substantially in a vertical plane, a substantially cylindrical supply reel 87 (supply portion) and take-up reel 88 (take-up portion) rotatably disposed passing through this base 85, a support arm 89 fixed to the base 85 and rotatably supporting the supply reel 87 and take-up reel 88, and a substantially long strip-shaped lock arm 92 which is connected to the rotating pin 91 that passes through a lower end side region of the base 85, and which is rotatable around the rotating pin 91 substantially in the direction along the surface of the base 85. The cassette member 73 is mounted to the device body 72 by each of the reels 87, 88 fitting onto the rotating shafts 75, 76 on the side of the device body 72.

A through-hole 93 is formed in a location between the supply reel 87 and the take-up reel 88 in the base 85. This through-hole 93 is formed with an inside diameter and in a location such that the tip portion 83 of the engaging pin 81 is able to pass through it when the cassette member 73 is mounted on the device body 72.

The supply reel 87 is such that the tape 23 that is unused is wound therearound, and is formed substantially cylindrical having an inside diameter enabling it to fit onto the free rotatable rotating shaft 75. Meanwhile, the take-up reel 88 is such that the tape 23 that has been reeled out from the supply reel 87 is wound therearound, and is substantially cylindrical having an inner diameter enabling it to fit onto the rotating shaft 76 rotated by means of the stepping motor 55. Therefore, when the stepping motor 55 is driven and the rotating shaft 76 and the driving roller 61 are rotated in the state in which each reel 87, 88 is fit onto the rotating shafts 75, 76, the supply reel 87 and the take-up reel 88 rotate simultaneously, such that the tape 23 is reeled out from the supply reel 87 and wound up on the take-up reel 88.

The lock arm 92 is such that the rotating pin 91 is connected to the lower end side while a rod-shaped knob 94 protruding on the forward side is formed on the upper end side. Below this knob 94 is formed a notch 95 which opens to the take-up reel 88 side. This notch 95 is formed engagable with the neck portion 83A of the engaging pin 81 when the cassette member 73 is fitted onto the device body 72 so as to prevent the cassette member 73 from falling off unintentionally. Note that one end side of the coil spring 96, of which other end side is fixed to the base 85, is fixed on the back side of the lock arm 92. Accordingly, the lock arm 92 is urged such that the upper portion side thereof rotates in a clockwise direction in FIG. 6.

Next, attachment procedure of the cassette member 73 will be described.

In the initial state, the cassette member 73 is such that the unused tape 23 is wound around the supply reel 87 and the tape 23 is strung around the lower end side of the rotating pin 91 protruding on the back side (the back side as viewed in FIG. 6) of the base 85, and the lead end side thereof is fixed to the take-up reel 88. From this state, the knob 94 of the lock arm 92 is pinched with fingers and, while holding the lock arm 92 in a position shown by the alternate long and two short dashes line in FIG. 6, the support arm 89 is held and each reel 87, 88 is fitted onto the rotating shafts 75, 76. In this state, when the fingers are released from the knob 94, the urging force of the coil spring 96 causes the lock arm 92 to rotate to a position of the solid line in the same figure such that the notch 95 and the neck portion 83A of the engaging pin 81 engage. This holds the cassette member 73 so that it will not fall off of the device body 72. Attachment of the tape 23 to the device body 72 is completed by pulling a portion of the tape 23 strung around the lower end side of the rotating pin 91 further downward with the fingers and catching it on the tip of the plate-shaped member 56 positioned on the lower end side of the movable base plate 42 at around this time.

Note that measurement of the adhesive strength of the sample 15 with the tape 23 attached in the above manner is conducted just as it is in the second embodiment.

Then, when the entire contact surface of the tape 23 has been used to measure the sample 15 and the tape 23 is nearly all wound on the take-up reel 88, the cassette member 73 is taken off of the device body 72 by the reverse operation as that mentioned above and it is replaced with a new cassette member 73.

Therefore, according to the aforementioned third embodiment, it is possible to easily replace the tape 23.

In the first through third embodiments, a roller-shaped roller 11 or a plate-shaped member 56 was employed as the guide member; however, it is not particularly limited to these and an object of other material, shape etc. may be used as long as there is no inconvenience with actual detection.

Note that in each of the aforementioned embodiments the brake mechanism of the tape 23 is such as to be effective on the supply reels 19, 51 and take-up reels 21, 52; however the position is not particularly limited as long as the tape 23 is able to be inhibited from moving.

Also, to prevent as much as possible unintentional movement of the sample 15 during adhesive strength measuring without providing a sample holder 13, 57 in each of the above embodiments, the structure may be such that the adhesive strength of the sample 15 is measured holding the sample 15 with only the roller 11 or the plate-shaped member 56.

Further, the measurement means is not limited to the load cell 25 and may be another measurement means. For example, it is also possible to film from the pressing of the tape 23 to the sample 15 to the peeling of the tape 23 from the sample 15 and to detect the peeling time and distance between the sample 15 and the tape 23 abutting against the roller 11 or the plate-shaped member 56 when the sample 15 separates by image processing the number of pixels and the like obtained at that time, and to measure the adhesive strength of the sample 15 according to this distance and peeling time.

Also, in each of the foregoing embodiments, the adhesive strength of the sample 15 was measured by moving the tape 23 and pressing the unused portion of the contact surface thereof to the adhesive surface 15A of the sample 15. Conversely, however, the adhesive strength of the sample 15 may also be measured by moving the sample 15 and pressing the unused portion of the contact surface of the tape 23 to the adhesive surface 15A thereof.

As described above, according to the present invention, it is possible to accurately measure the adhesive strength of a sample without contaminating the tape.

Industrial Applicability

The present invention may be applied, for example, as a method and device to measure adhesive strength of a sample of rubber or the like.

What is claimed is:

1. An adhesive strength measuring device for measuring an adhesive strength of a sample by pressing a predetermined point of a guide member provided with a predetermined contact surface to the sample, then peeling the pressed contact surface, and measuring the adhesive strength, said device comprising:

a vertically moveable base plate;

a load cell connected to said vertically movable base plate to measure adhesive strength;

a guide member connected to said vertically movable base plate;

a moving mechanism connected to said vertically movable base plate, wherein said moving mechanism is adapted to move an unused portion of the contact surface to a position at which said guide member can press an unused portion of the contact surface to the sample to enable each measurement of the adhesive strength; and a sample holding mechanism for holding the sample, wherein the sample holding mechanism is provided so as to be able to be raised and lowered at the same time as the guide member, and is also provided so as to be able to be raised and lowered relative to the guide member via an urging device for urging in a direction away from the guide member.

2. An adhesive strength measuring device for measuring an adhesive strength of a sample by pressing a predetermined point of a guide member provided with a predetermined contact surface to the sample, then peeling the pressed contact surface, and measuring the adhesive strength, said device comprising:

a vertically moveable base plate;

a load cell connected to said vertically movable base plate to measure adhesive strength;

a guide member connected to said vertically movable base plate, wherein the guide member is held by a cassette member which is attachable and detachable with respect to a device body;

a moving mechanism connected to said vertically movable base plate, wherein said moving mechanism is adapted to move an unused portion of the contact surface to a position at which said guide member can press an unused portion of the contact surface to the sample to enable each measurement of the adhesive strength.

3. An adhesive strength measuring device for measuring an adhesive strength of a sample by pressing a predetermined point of a guide member provided with a predetermined contact surface to the sample, then peeling the pressed contact surface, and measuring the adhesive strength, said device comprising:

a vertically movable base plate;

a load cell connected to said vertically movable base plate;

a guide member connected to said load cell, wherein said guide member is adapted to press an unused portion of the contact surface to the sample and said load cell is adapted to measure the pressure force of the guide member;

a moving mechanism connected to said vertically movable base plate, wherein said moving mechanism is adapted to move an unused portion of the contact surface to a position at which said guide member can press an unused portion of the contact surface to the sample; and a sample holding mechanism for holding the sample, wherein the sample holding mechanism is provided so as to be able to be raised and lowered at the same time as the guide member, and is also provided so as to be able to be raised and lowered relative to the guide member via an urging device for urging in a direction away from the guide member.

4. An adhesive strength measuring device for measuring an adhesive strength of a sample by pressing a predetermined point of a guide member provided with a predetermined contact surface to the sample, then peeling the pressed contact surface, and measuring the adhesive strength, said device comprising:

a vertically movable base plate;

a load cell connected to said vertically movable base plate;

a guide member connected to said load cell, wherein said guide member is adapted to press an unused portion of the contact surface to the sample and said load cell is adapted to measure the pressure force of the guide member, wherein the guide member is held by a cassette member which is attachable and detachable with respect to a device body; and a moving mechanism connected to said vertically movable base plate, wherein said moving mechanism is adapted to move an unused portion of the contact surface to a position at which said guide member can press an unused portion of the contact surface to the sample.

* * * * *